United States Patent [19]
Watanabe et al.

[11] Patent Number: 4,812,562
[45] Date of Patent: Mar. 14, 1989

[54] CEPHALOSPORIN DERIVATIVES

[75] Inventors: Yoshiaki Watanabe, Tokyo; Chihiro Yokoo, Gyoda; Masami Goi, Kitasaitama; Akira Onodera, Kuki; Mitsuo Murata, Kitakatsushika; Hiroshi Fukushima, Minamisaitama; Kaoru Sota, Tokorozawa, all of Japan

[73] Assignee: Taisho Pharmaceutical Co., Ltd., Japan

[21] Appl. No.: 887,941

[22] Filed: Jul. 22, 1986

[30] Foreign Application Priority Data

Jul. 25, 1985 [JP] Japan .................. 60-164664

[51] Int. Cl.$^4$ .................. C07D 501/36; A61K 31/545
[52] U.S. Cl. ..................................... 540/227; 540/226
[58] Field of Search ............... 540/227, 226; 514/206, 514/204

[56] References Cited

U.S. PATENT DOCUMENTS

| | | |
|---|---|---|
| 4,452,851 | 6/1984 | Takaya et al. ............ 424/246 |
| 4,462,999 | 7/1984 | Takaya et al. ............ 540/227 |
| 4,593,022 | 6/1986 | Labeew et al. ............ 516/206 |
| 4,609,654 | 9/1986 | Labeew et al. ............ 514/206 |
| 4,631,274 | 12/1986 | Takaya et al. ............ 514/202 |
| 4,699,981 | 10/1987 | Natanabe et al. .......... 540/227 |

FOREIGN PATENT DOCUMENTS

| | | |
|---|---|---|
| 0182301 | 5/1986 | European Pat. Off. . |
| 3518848A1 | 11/1985 | Fed. Rep. of Germany . |
| 2381052 | 2/1978 | France . |
| 1599722 | 10/1981 | Japan . |
| 2144420A | 3/1985 | United Kingdom . |

OTHER PUBLICATIONS

Chemical Abstracts vol. 105; 42547(a) (1986).

*Primary Examiner*—Nicholas S. Rizzo
*Attorney, Agent, or Firm*—Lorusso & Loud

[57] ABSTRACT

Cephalosporin derivatives represented by the general formula

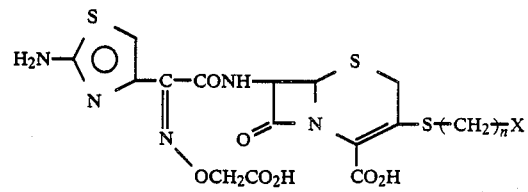

wherein X represents a halogen atom, a hydroxyl group, a cyano group, a trifluoromethyl group, an amino group, a lower alkylcarbonylamino group, a lower alkoxy group, a lower alkylthio group, a lower alkoxycarbonyl group, a carbamoyl group, a substituted carbamoyl group, a carbamoyloxy group, a lower alkylcarbonyl group, a lower alkenyl group, an ethynyl group, a thiocyanate group, an α-carboxyaminomethyl group, a phenyl group, a pyridinyl group or an aminothiazolyl group, and n is an integer of 1 to 3, and the non-toxic salts thereof, are disclosed. These compounds are useful as antibacterial agents.

7 Claims, No Drawings

CEPHALOSPORIN DERIVATIVES

BACKGROUND OF THE INVENTION

1. Field of the Invention

The present invention relates to novel cephalosporin derivatives for oral administration, and more particularly to cephalosporin derivatives and their non-toxic salts showing excellent antibacterial effect by oral administration.

2. Description of the Prior Art

Cephalosporin drugs are widely used for the treatment and prevention of various infectious diseases caused by pathogenic bacteria.

Especially, since the cephalosporin drugs for oral administration, represented by cefalexin, can be more easily used than the one for injectional administration, they are most widely used now. Furthermore, the compounds having an alkylthio group at the 3-position of cephalosporin derivative are disclosed more recently (U.S. Pat. No. 4,452,851).

However, known cephalosporin drugs for oral administration are much inferior to the one for injectional administration in terms of antibacterial activity and antibacterial spectrum, and the problem is the remarkable increase of strains resistant to these drugs.

Under such circumstances, it is desired to find cephalosporin drugs having excellent antibacterial activity, wide antibacterial spectrum, and effective amount in the blood concentration.

SUMMARY OF THE INVENTION

As a result of the earnest studies for the purpose of finding of cephalosporin derivatives showing strong antibacterial activity, wide antibacterial spectrum and high blood concentration when administered orally, the present inventors found some cephalosporin derivatives showing antibacterial activity, antibacterial spectrum and blood concentration superior to cefalexin, and completed the present invention.

The compounds of the present invention are cephalosporin derivatives represented by the general formula

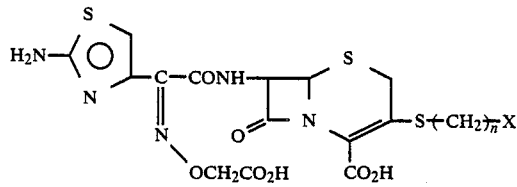

wherein X represents a halogen atom, a hydroxyl group, a cyano group, a trifluoromethyl group, an amino group, a lower alkylcarbonylamino group, a lower alkoxy group, a lower alkylthio group, a lower alkoxycarbonyl group, a carbamoyl group, a substituted carbamoyl group, a carbamoyloxy group, a lower alkylcarbonyl group, a lower alkenyl group, an ethynyl group, a thiocyanate group, an α-carboxyaminomethyl group, a phenyl group, a pyridinyl group or an aminothiazolyl group, and n is an integer of 1 to 3, and the non-toxic salts thereof.

DETAILED DESCRIPTION OF THE INVENTION

The term "lower" used in relation to the alkyl group, alkoxy group and other functional groups means those having 1 to 6 carbon atoms in straight and branched chain. For example, the lower alkylcarbonylamino group refers to an acetylamino group, a propionylamino group and the like; the lower alkoxy group refers to a methoxy group, an ethoxy group, a n-propoxy group, an isopropoxy group, a n-butoxy group, an isobutoxy group, a pentyloxy group and the like; the lower alkylthio group refers to a methylthio group, an ethylthio group, a propylthio group and the like; the lower alkoxycarbonyl group refers to a methoxycarbonyl group, an ethoxycarbonyl group, a n-propoxycarbonyl group, an isopropoxycarbonyl group and the like; the lower alkylcarbonyl group refers to an acetyl group, a propionyl group, a butyryl group and the like; and the lower alkenyl group refers to a vinyl group, a 1-propenyl group, a 2-methyl-1-propenyl group, a 1-butenyl group and the like.

The halogen atom refers to a fluorine atom, a chlorine atom, a bromine atom and an iodine atom.

The substituted carbamoyl group refers to an N,N-dimethylcarbamoyl group, an N,N-diethylcarbamoyl group, an N-methylcarbamoyl group, an N-ethylcarbamoyl group and the like.

The non-toxic salts of the compound of Formula I of the invention mean those which are pharmaceutically acceptable, for example, salts with inorganic bases including sodium, potassium, calcium and magnesium; salts with organic bases such as ammonia, triethylamine and cyclohexylamine; salts with basic amino acids such as arginine and lysine; salts with mineral acids such as sulfuric acid, hydrochloric acid and phosphoric acid; and organic acids such as acetic acid, lactic acid, tartaric acid, fumaric acid, maleic acid, trifluoroacetic acid and methanesulfonic acid.

Among the preferred compounds of Formula I, are included the compounds, wherein X is a cyano group, a carbamoyl group, a carbamoyloxy group, a fluorine atom, an amino group, a methoxy group or a pyridinyl group.

The compounds of the present invention are those in the forms of geometric isomers [E-form and Z-form] derived from the oxyimino group at the 7-position side chain, and both isomers are included within the scope of the present invention, but the Z-form is preferred.

The compounds of Formula I of the present invention can be, for example, obtained according to the following synthetic methods.

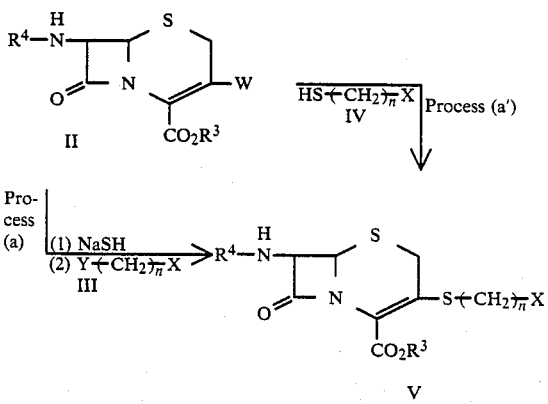

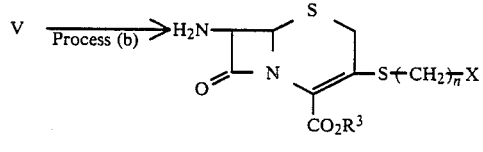

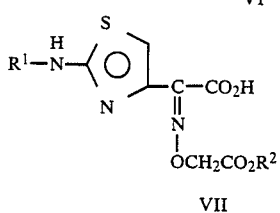

VII

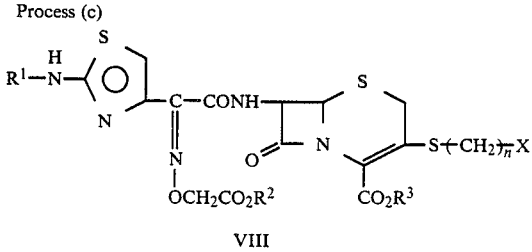

VIII

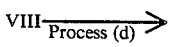

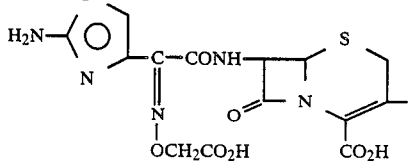

I

In the scheme mentioned above, $R^1$ represents a protecting group of the amino group, $R^2$ and $R^3$ represent each a protecting group of the carboxyl group, X and n are as defined above, $R^4$ represents a protecting group of the amino group such as a phenylacetyl group, a phenoxyacetyl group, a trityl group, a phthaloyl group, a formyl group, a benzoyl group and the like, W represents a halogen atom (e.g., a chlorine atom, a bromine atom or an iodine atom), a methanesulfonyloxy group, a trifluomethanesulfonyloxy group, a diphenylphosphoryloxy group, a p-toluenesulfonyloxy group and the like, and Y represents an eliminating group such as a halogen atom (e.g., a chlorine atom, a bromine atom or an iodine atom), a trifluoroethanesulfonyloxy group, a methanesulfonyloxy group, a p-toluenesulfonyloxy group and the like.

The protecting groups of the amino group and carboxyl group such as $R^1$, $R^2$ and $R^3$ are those frequently used in the field of the β-lactam chemistry. For example, $R^1$ is a trityl group, a monochloroacetyl group, a formyl group, a p-methoxybenzyloxycarbonyl group and the like, $R^2$ and $R^3$ are each a benzhydryl group, a p-methoxybenzyl group, a p-nitrobenzyl group, a benzyl group, a 2,2,2-trichloroethyl group, a trimethylsilyl group, an allyl group and the like.

Process (a): A known compound of the Formula II is dissolved in a reaction-inert organic solvent, and reacted with 1.0 to 1.2 molar equivalents of sodium hydrosulfide in the presence of a base. The reaction temperature is from −50° C. to 100° C., preferably from −25° C. to 5° C. The reaction time is from 10 minutes to 4 hours, preferably from 10 minutes to one hour. The resulting compound, in the same reaction system (or after isolation), is reacted with 1.0 to 2.0 molar equivalents of the compound of Formula III at a reaction temperature from −50° C. to 100° C., preferably −25° C. to 50° C. to give a 3-thio substituent of Formula V. The reaction time depends on the kinds of the base and the compound of Formula III which are used, and the reaction temperature, but it is in the range of 10 minutes to 5 hours, usually 10 minutes to 2 hours. Preferred solvents in this reaction are, N,N-dimethylformamide, N,N-dimethylacetamide, dimethyl sulfoxide, hexamethylphosphorotriamide, acetonitrile, tetrahydrofuran, dichloromethane and the like. The preferred base is an organic base such as diisopropylethylamine, triethylamine, N,N-dimethylaminopyridine, N,N-dimethylaniline and the like. The most preferred amount of the base is from 1.0 to 2.0 molar equivalents relative to the compound of Formula II.

Process (a'): To a solution of the Compound II in a reaction-inert organic solvent is added, in the presence of a base, 1.0 to 1.5 molar equivalents of the compound of Formula IV in the form of a solid or a solution in the same organic solvent as described above for carrying out the reaction. The reaction temperature is from −50° C. to 50° C., preferably −10° C. to 5° C. The reaction time depends upon the kinds of the base and the the compound of Formula IV which are used and the reaction temperature, but it is in the range of 10 minutes to 20 hours, usually 30 minutes to 2 hours. Preferred solvents used in this reaction are acetonitrile, N,N-dimethylformamide, N,N-dimethylacetamide, dimethyl sulfoxide, hexamethylphosphorotriamide, tetrahydrofuran, dichloromethane, benzene and the like. Preferred bases used are organic bases such as diisopropylethylamine, triethylamine, N,N-dimethylaminopyridine, N,N-dimethylaniline and the like. The most preferred amount of the base is from 1.0 to 2.0 molar equivalents relative to the Compound II.

Process (b): The protecting group $R^4$ at the 7-position of the compound of Formula V obtained in the above process (a) or (a') can be eliminated by the method frequently used in the field of the β-lactam chemistry to give the compound of Formula VI. For example, the compound of Formula V wherein the protecting group $R^4$ is a phenoxyacetyl group, a phenylacetyl group or a benzoyl group, is stirred in a reaction solvent of dichloromethane or benzene in the presence of 1.5 to 2.0 molar equivalents of phosphorus pentachloride and 2.0 to 3.0 molar equivalents of pyridine at −40° C. to 30° C. for 30 minutes to 3 hours, thereafter a large excess amount of methanol is added at −50° C. to 20° C., and the mixture is stirred for 30 minutes to 2 hours and then treated with a large excess amount of water at −50° C. to 20° C. for 30 minutes to one hour to give the compound of Formula VI.

Furthermore, the compound of Formula V wherein the protecting group $R^4$ is a trityl group, is dissolved in a reaction-inert solvent (e.g., ethyl acetate), 1.0 to 1.5 molar equivalents of p-toluenesulfonic acid monohydrate is added under ice-cooling, and the mixture is stirred for 1 to 5 hours to give the compound of Formula VI in the form of p-toluenesulfonic acid salt. If necessary, the p-toluenesulfonic acid salt is treated with a base to give the compound of Formula VI in the form of the free base.

Process (c): In order to obtain the compound of Formula VIII from the compound of Formula VI, the compound of Formula VI is reacted with the 2-aminothiazoleacetic acid derivative of Formula VII in the presence of a condensing agent or reacted with a reactive derivative of the compound of Formula VII. Examples of the condensing agent are N,N'-dicyclohexylcarbodiimide, 1-ethoxycarbonyl-2-ethoxy-1,2-dihydroquinoline, N,N'-carbonyldiimidazole, diphenylphosphoryl azide, Vilsmeier reagent and the like. Examples of the above reactive derivative of the compound of Formula VII are the acid halides (e.g., acid chloride and acid bromide), acid anhydride (e.g., symmetrical acid anhydrides of the compound of Formula VII, and mixed acid anhydrides with ethyl carbonate, diphenylphosphoric acid, methanesulfonic acid and the like), and activated esters (e.g., esters with p-nitrophenol, thiophonyl, N-hydroxysuccinimide and the like). Referring to the acid chloride as the reactive derivative of the compound of Formula VII, first the compound of Formula VII is dissolved in a reaction-inert solvent, 1.0 to 1.1 molar equivalents of phosphorus pentachloride is added in the presence of a base at $-30°$ C. to $-10°$ C., and the mixture is stirred for 10 to 30 minutes to give an acid chloride of the compound of Formula VII. To the compound is added a solution of 0.7 to 1.0 molar equivalent of the compound of Formula VI in the same reaction-inert solvent as those mentioned above in the range of $-30°$ C., and the mixture was stirred for 10 to 30 minutes to give the compound of Formula VIII. Preferred solvents used in this process are dichloromethane, chloroform, N,N-dimethylformamide, acetonitrile and the like. Preferred bases are pyridine, N,N-dimethylaniline, N,N-dimethylaminopyridine, triethylamine, diisopropylethylamine and the like. The amount of the base used is 4.0 to 5.5 molar equivalents relative to the compound of Formula VI.

Process (d): The protecting groups of the compound of Formula VIII are eliminated by the method frequently used in the field of the β-lactam chemistry, for example, by a method using trifluoroacetic acid-anisole to give the compound of Formula I. In this method, the compound of Formula VIII is reacted with a large excess amount of trifluoroacetic acid-anisole (volume ratio, 5:1) in a reaction-inert solvent or in the absence of solvent for 30 minutes to one hour, preferably at $-5°$ C. to 25° C.

The compounds of Formula I of the present invention show not only strong antibacterial activity against various pathogenic bacteria but also high absorption by oral administration, therefore these compounds are useful as antibacterial agents for oral administration. For this purpose, they are administered orally in a conventional dosage form such as tablets, capsules, granules and the like which can be prepared according to usual pharmaceutical practices. In the above preparations are included conventional additives such as fillers, binding agents, disintegrators, vehicles, pH adjusting agents, solubilizers and the like.

Although the dosage of the compounds of the present invention depends on the age and conditions of the patient, the usual dosage is from 200 mg to 400 mg per person per day.

Subsequently, there were tested the minimal inhibitory concentration (MIC) of the compounds of the present invention against various bacteria and the concentration of the compound in blood after oral administration to rats, and the results are shown.

TEST 1

The antibacterial activities of the compound of the present invention against various bacteria (inoculum size: $10^6$ cells/ml) were tested by the agar plate dilution method, and the results are shown in the following Table 1.

TABLE 1

| Bacteria | MIC (μg/ml) Compound | | | | | | | | |
|---|---|---|---|---|---|---|---|---|---|
|  | A | B | C | D | E | F | G | XX | YY |
| Escherichia coli NIHJ JC-2 | 1.56 | 0.78 | 1.56 | 0.78 | 0.39 | 1.56 | 0.39 | 1.56 | 12.5 |
| Klebsiella pneumoniae T 25 | 25 | 6.25 | 25 | 3.13 | 1.56 | 12.5 | 6.25 | 25 | 100 |
| Morganella morganii IID 602 | <0.1 | ≦0.1 | <0.1 | 0.39 | ≦0.1 | 0.1 | ≦0.1 | 0.39 | 200 |
| Serratia marcescens IID 618 | 0.78 | 1.56 | 1.56 | 0.39 | 0.78 | 0.78 | 0.78 | 1.56 | >400 |
| Staphylococcus aureus FDA 209P-JC | 6.25 | 25 | 6.25 | 6.25 | 12.5 | 12.5 | 12.5 | 50 | 0.78 |
| Bacillus cereus S 1101 | 0.2 | 0.39 | 0.2 | 0.2 | 0.39 | 0.2 | 0.2 | 0.78 | ≦0.1 |

Note
A: The compound obtained in Example 4
B: The compound obtained in Example 6
C: The compound obtained in Example 9
D: The compound obtained in Example 10
E: The compound obtained in Example 21
F: The compound obtained in Example 24
G: The compound obtained in Example 27
XX: 7β-{α-(2-aminothiazole-4-yl)-α-[(Z)-carboxy-methoxyimino]acetamido}-3-methylthio-3-cephem-4-carboxylic acid sodium salt (previously known compound)
YY: Cefalexin (previously known compound)

TEST 2

Male wister rats (7 weeks old) were administered orally with the test compound, and the change of the concentration of the compound in blood was measured.
Dosage of the test compound: 50 mg/kg
Quantitative method: Bioassy
(test bacterium: Escherichia coli SC507)
The results are shown in Table 2.

| | Concentration in blood (μg/ml) | | | |
|---|---|---|---|---|
| | Test compound | | | |
| Time | A | C | D | YY |
| 1.0 hour | 28.7 | 25.6 | 11.9 | 14.8 |
| 2.0 hours | 19.5 | 9.1 | 16.6 | 11.2 |
| 4.0 hours | 4.3 | 4.0 | 15.4 | 3.1 |

Note
A, C, D and YY are as defined above.

The present invention is illustrated in more detail by the following Examples but is not limited thereto.

EXAMPLE 1

(a) To a cooled (−10° C.) solution of 748 mg (1 mM) of benzhydryl 7β-phenoxyacetamido-3-diphenylphosphoryloxy-3-cephem-4-carboxylate in 6 ml of N,N -dimethylformamide were added a solution of 88 mg (1.1 mM) of 70% sodium hydrosulfide in 4 ml of N,N-dimethylformamide and 194 mg (1.5 mM) of diisopropylethylamine, and the mixture was stirred at the same temperature for 30 minutes. To the reaction mixture was added 242 mg (2 mM) of allyl bromide, and the mixture was stirred for 10 minutes. After the reaction, ethyl acetate (50 ml) was added, washed with 0.5% hydrochloric acid (30 ml) and a saturated aqueous sodium chloride solution (30 ml×2), successively, and dried over anhydrous magnesium sulfate. The solvent was evaporated, and the residue was purified by silica gel column chromatography (eluent; benzene:acetone=20:1 to 15:1) to give 520 mg of benzhydryl 7β-phenoxyacetamido-3-allylthio-3-cephem-4-carboxylate.

NMR(CDCl$_3$)δ(ppm): 3.30(2H, d, J=7Hz), 3.39(1H, d, J=17Hz), 3.47(1H, d, J=17Hz), 4.59(2H, s), 5.03(1H, d, J=5Hz), 5.10-5.24(2H, m), 5.63-5.82(1H, m), 5.74(1H, dd, J=9Hz, 5Hz), 6.90-7.08(4H, m), 7.25-7.61(13H, m).

IR $\nu_{max}^{KBr}$ cm$^{-1}$ 3280, 1770, 1760, 1510.

(b) To a solution of 520 mg (0.91 mM) of benzhydryl 7β-phenoxyacetamido-3-allylthio-3-cephem-4-carboxylate, obtained in the above (a), in 8.5 ml of dry benzene were added 145 mg (1.82 mM) of pyridine and 285 mg (1.36 mM) of phosphorus pentachloride at room temperature, and the mixture was stirred for 2 hours. Subsequently, 2 ml of dry methanol (2 ml) was added under ice-cooling, and the mixture was stirred for one hour. And then water (2 ml) was added and the mixture was stirred for one hour. After the reaction, the mixture was made weakly basic with a saturated aqueous sodium bicarbonate solution and extracted with ethyl acetate (50 ml). The ethyl acetate layer was washed with a saturated sodium chloride solution (30 ml) and dried over anhydrous magnesium sulfate. The solvent was evaporated, and the residue was purified by silica gel column chromatography (eluent; first dichloromethane and then dichloromethane:methanol=50:1) to give 262 mg of benzhydryl 7β-amino-3-allylthio-3-cephem-4-carboxylate.

(c) To a cooled (−10° C.) solution of 426 mg (0.65 mM) of α-(2-tritylaminothiazole-4-yl)-α-[(Z)-benzhydryloxycarbonylmethoxyimino]acetic acid in 10 ml of dry dichloromethane were added 258 mg (3.25 mM) of pyridine and 136 mg (0.65 mM) of phosphorus pentachloride, and the mixture was stirred for 20 minutes. Subsequently, 3 ml of a solution of 260 mg (0.59 mM) of the 7-amino form, obtained in the above (b), in 3 ml of dry dichloromethane was added at the same temperature, and the mixture was stirred for 20 minutes. After the reaction, ethyl acetate (50 ml) was added, and the mixture was washed with 0.5% hydrochloric acid (20 ml) and a saturated aqueous sodium chloride solution (30 ml), successively, and dried over anhydrous magnesium sulfate. The solvent was evaporated, and the residue was purified by silica gel column chromatography (eluent; benzene:acetone=20:1 to 15:1) to give 333 mg of benzhydryl 7β-{α-(2-tritylaminothiazole-4-yl)-α-[(Z)-benzhydryloxycarbonylmethoxyimino]acetamido}-3-allylthio-3-cephem-4-carboxylate.

NMR(CDCl$_3$)δ(ppm): 3.25(1H, d, J=17Hz), 3.26-3.40(2H, m), 3.40(1H, d, J=17Hz), 4.94(1H, d, J=17Hz), 5.01(1H, d, J=5Hz), 5.06(1H, d, J=17Hz), 5.10-5.22(2H, m), 5.64-5.77(1H, m), 5.81(1H, dd, J=9Hz, 5Hz), 6.84(1H, s), 6.96(2H, s), 7.01(1H, bs), 7.23-7.55(35H, m), 8.15(1H, d, J=9Hz).

(d) To a mixture of trifluoroacetic acid (4 ml) and anisole (0.8 ml) was added under ice-cooling 320 ml (0.30 mM) of benzhydryl-7β-{α-(2-tritylaminothiazole-4-yl) -α-[(Z)-benzhydryloxycarbonylmethoxyimino]acetamido}-3-allylthio-3-cephem-4-carboxylate obtained in the above (c), and the mixture was stirred for 45 minutes. The reaction mixture was slowly added dropwise to a mixture of diethyl ether and n-hexane (1:2, 40 ml), and the crystals which formed were collected by filtration to give 180 mg of the desired trifluoroacetate. Then, the crystals, together with 76 mg (0.90 mM) of sodium bicarbonate, were dissolved in 5 ml of water and purified by Sephadex LH-20 column chromatography (eluent: water) to give 140 mg of 7β-{α-(2-aminothiazole-4-yl)-α-[(Z)-carboxymethoxyimino]acetamido}-3-allythio-3-cephem-4-carboxylic acid sodium salt.

NMR(D$_2$O)δ(ppm): 3.34-3.54(2H, m), 3.52(1H, d, J=17Hz), 3.79(1H, d, J=17Hz), 4.59(2H, s), 5.10-5.28(2H, m), 5.25(1H, d, J=5Hz), 5.82(1H, d, J=5Hz), 5.78-6.00(1H, m), 7.08(1H, s).

IR $\nu_{max}^{KBr}$ cm$^{-1}$; 3340, 1755, 1580, 1525, 1385.

EXAMPLE 2

(a) To a cooled (−25° C.) solution of 1.47 g (1.72 mM) of benzhydryl 7β-tritylamino-3-diphenylphosphoryloxy-3-cephem-4-carboxylate in 15 ml of N,N-dimethylformamide were added a solution of 0.15 g (1.89 mM) of 70% sodium hydrosulfide in 5 ml of N,N-dimethylformamide and 0.33 g (2.58 mM) of diisopropylethylamine. The mixture was stirred at −20° to −15° C. for one hour, and 0.64 g (3.44 mM) of iodoacetamide was added at the same temperature, and the mixture was stirred for one hour. After the reaction, ethyl acetate (100 ml) was added, and the mixture was washed with 0.5% hydrochloric acid (50 ml) and a saturated aqueous sodium chloride solution (50 ml×2), successively, and dried over anhydrous magnesium sulfate. The solvent was evaporated, and the residue was purified by silica gel column chromatography (eluent; benzene: ethyl acetate=1:1) to give 0.56 g of benzhydryl 7β-tritylamino-3-carbamoylmethylthio-3-cephem-4-carboxylate.

NMR(CDCl$_3$) δ(ppm): 3.01(1H, d, J=10 Hz), 3.33(1H, d, J=17 Hz), 3.34(2H, bs), 3.48(1H, d, J=17 Hz), 4.30(1H, d, J=5 Hz), 4.75(1H, dd, J=10 Hz, 5 Hz), 5.28(1H, bs), 6.52(1H, bs), 6.95(1H, s), 7.20-7.54(25H, m).

(b) To a solution of 0.56 g (0.8 mM) of benzhydryl 7β-tritylamino-3-carbamoylmethylthio-3-cephem-4- carboxylate obtained in Example 2(a) in 10 ml of ethyl acetate, 0.18 g (0.96 mM) of p-toluenesulfonic acid monohydrate was added under ice-cooling, and the mixture was stirred for 4 hours. After the reaction, the white crystals which formed were collected by filtration to give 0.392 g of 7β-amino-3-carbamoylmethylthio-3-cephem-4-carboxylic acid benzhydryl ester p-toluenesulfonate.

NMR(DMSO-$d_6$) δ(ppm): 2.30(3H, s), 3.64(1H, d, J=16 Hz), 3.80(1H, d, J=16 Hz), 3.82(1H, d, J=16 Hz), 3.93(1H, d, J=16 Hz), 5.15(1H, d, J=5 Hz), 5.33(1H, d, J=5 Hz), 6.91(1H, s), 7.13(2H, d, J=8 Hz), 7.52(2H, d, J=8 Hz), 7.24–7.68(14H, m).

(c) To a solution of 465 mg (0.71 mM) of α-(2-tritylaminothiazol-4-yl)-α-[(Z)-benzhydryloxycarbonylmethoxyimino]acetic acid in 15 ml of dry dichloromethane was added 0.29 ml (3.58 mM) of pyridine. To the cooled (−30° to −20° C.) mixture was added 148 mg (0.71 mM) of phosphorus pentachloride, and the mixture was stirred for 30 minutes. To the mixture were added at the same temperature a solution of 364 mg (0.56 mM) of the 7-amino derivative p-toluenesulfonate obtained in Example 2(b) and 0.08 ml (0.56 mM) of triethylamine in 5 ml of dry dichloromethane, and the mixture was stirred for 30 minutes. Subsequently, following the procedure of Example 1(c) there was obtained 340 mg of benzhydryl 7β-{α-(2-tritylaminothiazole-4-yl)-α-[(Z)-benzhydryloxycarbonylmethoxyimino]acetamido}-3-carbamoylmethylthio-3-cephem-4-carboxylate.

NMR(CDCl$_3$) δ(ppm): 3.30(1H, d, J=17 Hz), 3,35(2H, bs), 3.51(1H, d, J=17 Hz), 4.92(1H, d, J=17 Hz), 5.02(1H, d, J=5 Hz), 5.03(1H, d, J=17 Hz), 5.33(1H, bs), 5.87(1H, dd, J=9 Hz, 5 Hz), 6.38(1H, bs), 6.80(1H, s), 6.96(2H, s), 7.02(1H, bs), 7.24–7.50(35H, m), 8.12(1H, d, J=9 Hz).

(d) To a mixture of trifluoroacetic acid (4 ml) and anisole (0.8 ml) was added under ice-cooling 320 mg (0.29 mM) of benzhydryl 7β-{α-(2-tritylaminothiazole-4-yl)-α-[(Z)-benzhydryloxycarbonylmethoxyimino]acetamido}-3-carbamoylmethylthio-3-cephem-4-carboxylate obtained in Example 2(c), and the mixture was stirred for 45 minutes. Subsequently, following the procedure of Example 1(d), there was obtained 160 mg of 7β-{α-(2-aminothiazole-4-yl)-α-[(Z)-carboxymethoxyimino]acetamido}-3-carbamoylmethylthio-3-cephem-4-carboxylic acid sodium salt.

NMR(D$_2$O) δ(ppm): 3.52(2H, s), 3.56(1H, d, J=17 Hz), 3.82(1H, d, J=17 Hz), 4.60(2H, s), 5.28(1H, d, J=5 Hz), 5.85(1H, d, J=5 Hz), 7.07(1H, s).

IR $\nu_{max}^{KBr}$ cm$^{-1}$; 3380, 1760, 1660–1670, 1600, 1530, 1390.

EXAMPLE 3

(a') To a solution of 857 mg (1 mM) of benzhydryl 7β-tritylamino-3-diphenylphosphoryloxy-3-cephem-4-carboxylate in 5 ml of acetonitrile was added a solution of 179 mg (1.5 mM) of N-acetylcysteamine in 2.5 ml of acetonitrile under ice-cooling, followed by addition of a solution of 194 mg (1.5 mM) of diisopropylethylamine in 2.5 ml of acetonitrile. After the reaction at the same temperature for 1.5 hours, ethyl acetate (100 ml) was added, and the mixture was washed with a saturated aqueous sodium chloride solution (100 ml×2) and dried over anhydrous magnesium sulfate. Subsequently, following the procedure of Example 1(a), there was obtained 580 mg of benzhydryl 7β-tritylamino-3-(2-acetylamino)ethylthio-3-cephem-4-carboxylate.

NMR(CDCl$_3$) δ(ppm): 1.81(3H, s), 2.57–2.93(2H, m), 2.98(1H, d, J=10 Hz), 3.08–3.44(3H, m), 3.45(1H, d, J=17 Hz), 4.32(1H, d, J=5 Hz), 4.72(1H, dd, J=10 Hz, 5 Hz), 6.40–6.51(1H, m), 6.93(1H, s), 7.16–7.56(25H, m).

IR $\nu_{max}^{KBr}$ cm$^{-1}$; 3340, 3280, 1770, 1715, 1650, 1520, 1485, 1440, 1360, 1265, 1205.

(b) To a solution of 540 mg (0.74 mM) of benzhydryl 7β-tritylamino-3-(2-acetylamino)-ethylthio-3-cephem-4-carboxylate obtained in Example 3 (a') in 7 ml of ethyl acetate was added 184 mg (0.97 mM) of p-toluenesulfonic acid mono-hydrate at room temperature, and the mixture was stirred for 4.5 hours. After the reaction, ethyl acetate (50 ml) was added, and the mixture was washed with a saturated aqueous sodium bicarbonate solution (50 ml) and a saturated aqueous sodium chloride solution (50 ml×2), successively, and dried over anhydrous magnesium sulfate. After drying, the solvent was evaporated and the residue was purified by silica gel column chromatography (eluent; chloroform:methanol=19:1) to give 309 mg of benzhydryl 7β-amino-3-(2-acetylamino)ethylthio-3-cephem-4-carboxylate.

NMR(CDCl$_3$) δ(ppm): 1.72(2H, bs), 1.82(3H, s), 2.61–2.77(1H, m), 2.84–2.99(1H, m), 3.09–3.29(1H, m), 3.35–3.53(2H, m), 3.64(1H, d, J=17 Hz), 4.77(1H, d, J=5 Hz), 5.01(1H, d, J=5 Hz), 6.54–6.69(1H, m), 7.01(1H, s), 7.18–7.47(10H, m).

IR $\nu_{max}^{KBr}$ cm$^{-1}$; 3400, 3040, 1760, 1735, 1610, 1545, 1350, 1210.

(c) Treating benzhydryl 7β-amino-3-(2-acetylamino)ethylthio-3-cephem-4-carboxylate obtained in Example 3(b) and α-(2-tritylaminothiazole-4-yl)-α-[(Z)-benzhydryloxycarbonylmethoxyimino]acetic acid according to the procedure of Example 1(c), there was obtained benzhydryl 7β-{α-(2-tritylaminothiazole-4-yl)-α-[(Z)-benzhydryloxycarbonylmethoxyimino]acetamido}-3-(2-acetylamino)ethylthio-3-cephem-4-carboxylate.

NMR(CDCl$_3$) δ(ppm): 1.83(3H, s), 2.62–2.93(2H, m), 3.07–3.48(3H, m), 3.50(1H, d, J=17 Hz), 4.94(1H, d, J=17 Hz), 5.04(1H, d, J=17 Hz), 5.06(1H, d, J=5 Hz), 5.87(1H, dd, J=9 Hz, 5 Hz), 6.37(1H, t, J=6 Hz), 6.81(1H, s), 6.96(1H, s), 6.98(1H, s), 7.03(1H, bs), 7.10–7.48(35H, m), 8.12(1H, d, J=9 Hz).

IR $\nu_{max}^{KBr}$ cm$^{-1}$; 3360, 1775, 1725, 1660, 1555, 1540, 1365, 1270, 1210.

(d) Treating benzhydryl 7β-{α-(2-tritylaminothiazole-4-yl)-α-[(Z)-benzhydryloxycarbonylmethoxyimino]acetamido}-3-(2-acetylamino)ethylthio-3-cephem-4-carboxylate obtained in Example 3(c) according to the procedure of Example 1(d), there was obtained 7β-{α-(2-aminothiazole-4-yl)-α-[(Z)-carboxymethoxyimino]acetamido}-3-(2-acetylamino)ethylthio-3-cephem-4-carboxylic acid sodium salt.

NMR(D$_2$O) δ(ppm): 1.99(3H, s), 2.70–3.06(2H, m), 3.26–3.48(2H, m), 3.54(1H, d, J=17 Hz), 3.80(1H, d, J=17 Hz), 4.60(2H, s), 5.29(1H, d, J=5 Hz), 5.82(1H, d, J=5 Hz), 7.08(1H, s).

IR $\nu_{max}^{KBr}$ cm$^{-1}$; 3300, 1755, 1655, 1590, 1525, 1350, 1195, 1175, 1035.

Following the procedure of Example 1, 2 or 3 using the corresponding compounds, there were obtained the following compounds indicated in Table 3 (wherein Me is a methyl group, Et is an ethyl group and C$_3$H$_7$-i is an isopropyl group).

TABLE 3

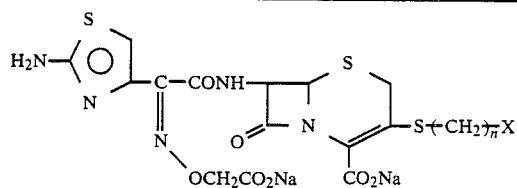

| Example No. | ‒(CH$_2$)$_n$X | NMR(D$_2$O) δ (ppm) | IR $\nu_{MAX}^{KBr}$ cm$^{-1}$ |
|---|---|---|---|
| 4 | —CH$_2$CN | 3.84(1H, d, J=17Hz) | 3360 |
| | | 3.96(1H, d, J=17Hz) | 2320 |
| | | 4.60(2H, s) | 1760 |
| | | 5.32(1H, d, J=5Hz) | 1600 |
| | | 5.88(1H, d, J=5Hz) | 1380 |
| | | 7.08(1H, s) | 1340–1350 |
| 5 | —CH$_2$CH$_2$CN | 2.80(2H, t, J=7Hz) | 3300 |
| | | 3.04(2H, m) | 2240 |
| | | 3.56(1H, d, J=17Hz) | 1755 |
| | | 3.88(1H, d, J=17Hz) | 1590 |
| | | 4.59(2H, s) | 1345 |
| | | 5.29(1H, d, J=5Hz) | |
| | | 5.85(1H, d, J=5Hz) | |
| | | 7.08(1H, s) | |
| 6 | —CH$_2$CH$_2$OMe | 2.98(2H, t, J=7Hz) | 3360 |
| | | 3.39(3H, s) | 1750–1760 |
| | | 3.56(1H, d, J=17Hz) | 1600 |
| | | 3.66(2H, t, J=7Hz) | 1385 |
| | | 3.86(2H, t, J=17Hz) | |
| | | 4.60(2H, s) | |
| | | 5.28(1H, d, J=5Hz) | |
| | | 5.84(1H, d, J=5Hz) | |
| | | 7.09(1H, s) | |
| 7 | —CH$_2$SMe | 2.20(3H, s) | 3300–3400 |
| | | 3.61(1H, d, J=17Hz) | 1760 |
| | | 3.88(1H, d, J=14Hz) | 1665 |
| | | 3.89(1H, d, J=17Hz) | 1610 |
| | | 4.00(1H, d, J=14Hz) | 1355 |
| | | 4.60(2H, s) | |
| | | 5.29(1H, d, J=5Hz) | |
| | | 5.84(1H, d, J=5Hz) | |
| | | 7.08(1H, s) | |
| 8 | —CH$_2$C≡CH | 3.51(1H, d, J=16Hz) | 3260 |
| | | 3.64(1H, d, J=16Hz) | 1760 |
| | | 3.68(1H, d, J=17Hz) | 1660 |
| | | 3.94(1H, d, J=17Hz) | 1600 |
| | | 4.60(2H, s) | 1530 |
| | | 5.30(1H, d, J=5Hz) | |
| | | 5.86(1H, d, J=5Hz) | |
| | | 7.09(1H, s) | |
| 9 | —CH$_2$CH$_2$F | 3.00–3.09(1H, m) | 3320 |
| | | 3.11–3.20(1H, m) | 1755 |
| | | 3.57(1H, d, J=17Hz) | 1650 |
| | | 3.87(1H, d, J=17Hz) | 1595 |
| | | 4.52(1H, t, J=7Hz) | 1350 |
| | | 4.60(2H, s) | |
| | | 4.77(1H, t, J=7Hz) | |
| | | 5.28(1H, d, J=5Hz) | |
| | | 5.84(1H, d, J=5Hz) | |
| | | 7.09(1H, s) | |
| 10 | —(CH$_2$)$_3$NH$_2$ | 1.86–2.01(2H, m) | 3380 |
| | | 2.80–2.90(2H, m) | 1755 |
| | | 3.13(2H, t, J=7Hz) | 1650 |
| | | 3.55(1H, d, J=17Hz) | 1600 |
| | | 3.80(1H, d, J=17Hz) | 1335 |
| | | 4.60(2H, s) | |
| | | 5.29(1H, d, J=5Hz) | |
| | | 5.83(1H, d, J=5Hz) | |
| | | 7.08(1H, s) | |
| 11 | —CH$_2$CO$_2$Me | 3.56(1H, d, J=17Hz) | 3360 |
| | | 3.57(1H, d, J=15Hz) | 1755 |
| | | 3.68(1H, d, J=15Hz) | 1650 |
| | | 3.76(3H, s) | 1600 |
| | | 3.86(2H, d, J=17Hz) | 1345 |
| | | 4.60(2H, s) | |
| | | 5.27(1H, d, J=5Hz) | |
| | | 5.84(1H, d, J=5Hz) | |
| | | 7.08(1H, s) | |
| 12 | —CH$_2$CO$_2$Et | 1.28(3H, t, J=7Hz) | 3380 |
| | | 3.55(1H, d, J=15Hz) | 1760 |

TABLE 3-continued

[Structure: H₂N-thiazole-C(=N-OCH₂CO₂Na)-CONH-cephem-CO₂Na with S-(CH₂)ₙ-X substituent]

| Example No. | —(CH₂)ₙX | NMR(D₂O) δ (ppm) | IR $\nu_{MAX}^{KBr}$ cm⁻¹ |
|---|---|---|---|
| | | 3.56(1H, d, J=17Hz) | 1715 |
| | | 3.67(1H, d, J=15Hz) | 1600 |
| | | 3.88(1H, d, J=17Hz) | 1390 |
| | | 4.23(2H, q, J=7Hz) | |
| | | 4.59(2H, s) | |
| | | 5.27(1H, d, J=5Hz) | |
| | | 5.84(1H, d, J=5Hz) | |
| | | 7.08(1H, s) | |
| 13 | —CH₂CO₂C₃H₇—i | 1.24(3H, s) | 3360 |
| | | 1.28(3H, s) | 1760 |
| | | 3.50(1H, d, J=15Hz) | 1600 |
| | | 3.58(1H, d, J=17Hz) | 1530 |
| | | 3.66(1H, d, J=15Hz) | 1390 |
| | | 4.59(2H, s) | |
| | | 5.02(1H, m) | |
| | | 5.27(1H, d, J=5Hz) | |
| | | 5.83(1H, d, J=5Hz) | |
| | | 7.08(1H, s) | |
| 14 | —CH₂SCN | 3.64(1H, d, J=17Hz) | 3380 |
| | | 3.99(1H, d, J=17Hz) | 2700 |
| | | 4.44(1H, d, J=14Hz) | 2200 |
| | | 4.54(1H, d, J=14Hz) | 1760 |
| | | 5.33(1H, d, J=5Hz) | 1600 |
| | | 5.89(1H, d, J=5Hz) | 1525 |
| | | 7.08(1H, s) | 1350 |
| 15 | —CH₂CON(Et)(Et) | 1.11(3H, t, J=7Hz) | 3340 |
| | | 1.21(3H, t, J=7Hz) | 1760 |
| | | 3.38(2H, q, J=7Hz) | 1600 |
| | | 3.46(2H, q, J=7Hz) | 1530 |
| | | 3.53(1H, d, J=17Hz) | 1380 |
| | | 3.65(1H, d, J=15Hz) | |
| | | 3.76(1H, d, J=15Hz) | |
| | | 3.88(1H, d, J=17Hz) | |
| | | 4.60(2H, s) | |
| | | 5.28(1H, d, J=5Hz) | |
| | | 5.84(1H, d, J=5Hz) | |
| | | 7.08(1H, s) | |
| 16 | —CH₂COCH₃ | 2.32(3H, s) | 3380 |
| | | 3.49(1H, d, J=17Hz) | 1760 |
| | | 3.78(1H, d, J=17Hz) | 1675 |
| | | 4.59(2H, s) | 1605 |
| | | 5.25(1H, d, J=5Hz) | 1530 |
| | | 5.83(1H, d, J=5Hz) | 1355 |
| | | 7.08(1H, s) | |
| 17 | —CH₂CF₃ | 3.30–3.68(2H, m) | 3360 |
| | | 3.58(1H, d, J=17Hz) | 1760 |
| | | 3.91(1H, d, J=17Hz) | 1600 |
| | | 4.60(2H, s) | 1390 |
| | | 5.28(1H, d, J=5Hz) | 1305 |
| | | 5.85(1H, d, J=5Hz) | |
| | | 7.08(1H, s) | |
| 18 | —CH₂CH=C(Me)(Me) | 1.68(3H, s) | 3440 |
| | | 1.73(3H, s) | 1770 |
| | | 3.32–3.60(2H, m) | 1640 |
| | | 3.54(1H, d, J=5Hz) | 1360 |
| | | 3.78(1H, d, J=5Hz) | |
| | | 4.60(2H, s) | |
| | | 5.24(1H, d, J=5Hz) | |
| | | 5.30(1H, t, J=8Hz) | |
| | | 5.80(1H, d, J=5Hz) | |
| | | 7.08(1H, s) | |
| 19 | —CH₂CH₂CO₂Me | 2.72(2H, t, J=7Hz) | 3280 |
| | | 3.02(2H, t, J=7Hz) | 1755 |
| | | 3.54(1H, d, J=17Hz) | 1580 |
| | | 3.72(3H, s) | 1345 |

TABLE 3-continued

Structure: H2N-thiazole-C(=N-OCH2CO2Na)-CONH-[β-lactam]-CO2Na with S-(CH2)n-X substituent

| Example No. | ─(CH₂)ₙ─X | NMR(D₂O) δ (ppm) | IR ν$_{MAX}^{KBr}$ cm⁻¹ |
|---|---|---|---|
| | | 3.84(1H, d, J=17Hz)<br>4.59(2H, s)<br>5.27(1H, d, J=5Hz)<br>5.83(1H, d, J=5Hz)<br>7.08(1H, s) | |
| 20 | ─CH₂CH₂CON(Et)(Et) | 1.10(3H, t, J=7Hz)<br>1.18(3H, t, J=7Hz)<br>2.73(2H, t, J=7Hz)<br>2.94–3.10(2H, m)<br>3.37(2H, q, J=7Hz)<br>3.42(2H, q, J=7Hz)<br>3.57(1H, d, J=17Hz)<br>3.85(1H, d, J=17Hz)<br>4.60(2H, s)<br>5.28(1H, d, J=5Hz)<br>5.82(1H, d, J=5Hz)<br>7.09(1H, s) | 3240<br>1750<br>1585<br>1525<br>1360 |
| 21 | ─CH₂─(2-pyridyl) | 3.16(1H, d, J=17Hz)<br>3.54(1H, d, J=17Hz)<br>4.03(1H, d, J=13Hz)<br>4.14(1H, d, J=13Hz)<br>4.58(2H, s)<br>5.13(1H, d, J=5Hz)<br>5.79(1H, d, J=5Hz)<br>7.06(1H, s)<br>7.32–7.42(1H, m)<br>7.50(1H, d, J=8Hz)<br>7.86(1H, t, J=8Hz)<br>8.47(1H, d, J=5Hz) | 3380<br>1750<br>1590<br>1525<br>1380<br>1345<br>1200 |
| 22 | ─CH₂─(2-amino-thiazol-4-yl) | 3.14(1H, d, J=17Hz)<br>3.57(1H, d, J=17Hz)<br>3.75(1H, d, J=14Hz)<br>3.90(1H, d, J=14Hz)<br>4.59(2H, s)<br>5.18(1H, d, J=5Hz)<br>5.80(1H, d, J=5Hz)<br>6.54(1H, s)<br>7.07(1H, s) | 3360<br>1755<br>1670<br>1600<br>1520<br>1390<br>1200 |
| 23 | ─CH₂─Ph | 3.27(1H, d, J=17Hz)<br>3.52(1H, d, J=17Hz)<br>3.97(1H, d, J=12Hz)<br>4.07(1H, d, J=12Hz)<br>4.58(2H, s)<br>5.11(1H, d, J=5Hz)<br>5.78(1H, d, J=5Hz)<br>7.06(1H, s)<br>7.30–7.47(5H, m) | 3360<br>1755<br>1655<br>1595<br>1530<br>1390<br>1200 |
| 24 | ─CH₂CH₂CONH₂ | 2.58(2H, t, J=7Hz)<br>3.00(2H, t, J=7Hz)<br>3.56(1H, d, J=17Hz)<br>3.85(1H, d, J=17Hz)<br>4.60(2H, s)<br>5.29(1H, d, J=5Hz)<br>5.84(1H, d, J=5Hz)<br>7.09(1H, s) | 3280<br>1750<br>1585<br>1340 |

TABLE 3-continued

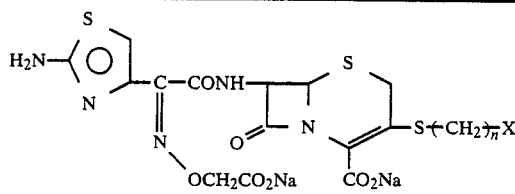

| Example No. | $\text{-}(CH_2)_{\overline{n}}X$ | NMR(D$_2$O) δ (ppm) | IR $\nu_{MAX}^{KBr}$ cm$^{-1}$ |
|---|---|---|---|
| 25 | (D) $-CH_2CH\begin{array}{c}NH_2\\CO_2Na\end{array}$ | 2.91(1H, dd, J=11Hz, 15Hz)<br>3.45(1H, dd, J=4Hz, 15Hz)<br>3.56–3.62(2H, m)<br>3.80(1H, d, J=17Hz)<br>4.59(2H, s)<br>5.31(1H, d, J=5Hz)<br>5.85(1H, d, J=5Hz)<br>7.08(1H, s) | 3380<br>1755<br>1650<br>1580<br>1555<br>1525<br>1385<br>1345<br>1195<br>1035 |

EXAMPLE 26

(a-1) To a solution of 16.5 g (31.3 mM) of p-methoxybenzyl 7β-phenylacetamido-3-methanesulfonyloxy-3-cephem-4-carboxylate in 70 ml of N,N-dimethylformamide were added a solution of 2.75 g (34.4 mM) of 70% sodium hydrosulfide in 30 ml of N,N-dimethylformamide and 6.06 g (47.0 mM) of diisopropylethylamine at −20° C., and the mixture was stirred at 0° C. for one hour. After the reaction, 1 l of water was added, the mixture was washed with ethyl acetate (200 ml×3), and the aqueous layer was adjusted to pH 1 with 3% hydrochloric acid and extracted with ethyl acetate (500 ml and 200 ml). The extract was washed with a saturated aqueous sodium chloride solution (300 ml×2) and dried over anhydrous magnesium sulfate. The solvent was evaporated, the residue was dissolved in 200 ml of dichloromethane, and the solution was added dropwise to 700 ml of diethyl ether with stirring. The precipitate formed was collected by filtration to give 7.24 g of p-methoxybenzyl 7β-phenylacetamido-3-mercapto-3-cephem-4-carboxylate.

(a-2) In 10 ml of N,N-dimethylformamide was dissolved 1.88 g (4 mM) of p-methoxybenzyl-7β-phenylacetamido-3-mercapto-3-cephem-4-carboxylate, and the solution was cooled to −20° C. To the solution were added 1.044 ml (6 mM) of diisopropylethylamine and 0.568 ml (8 mM) of ethylenebromohydrin, successively, and the mixture was stirred at 15° C. for one hour. The reaction mixture was poured into 50 ml of ice-waterand extracted with ethyl acetate (20 ml×3 ), and the extract was washed with a saturated aqueous sodium chloride solution (20 ml×3) and dried over anhydrous magnesium sulfate. Subsequently, the solvent was evaporated, and the residue was crystallized from diethyl ether to give 1.86 g of p-methoxybenzyl 7β-phenylacetamido-3-(2-hydroxy)ethylthio-3-cephem-4-carboxylate. m.p. 170°–172° C.

(a-3) In 30 ml of dichloromethane was dissolved 1.855 g (3.61 mM) of p-methoxybenzyl 7β-phenylacetamide-3-(2-hydroxy)ethylthio-3-cephem-4-carboxylate, and the solution was cooled to 0° C. To the solution were was added 1.51 ml (8.68 mM) of diisopropylethylamine and 0.576 ml (7.22 mM) of chloroacetyl chloride, successively, and the mixture was stirred at the same temperature for 30 minutes. The reaction mixture was washed with a saturated aqueous sodium chloride solution (10 ml×3) and dried over anhydrous magnesium sulfate. Subsequently, the solvent was evaporated, and the residue was purified by silica gel column chromatography (eluent; dichloromethane) to give 1.70 g of p-methoxybenzyl 7β-phenylacetamido-3-(2-chloroacetyloxy)ethylthio-3-cephem-4-carboxylate.

(b) In 50 ml of dry dichloromethane was dissolved 1.70 g (2.88 mM) of p-methoxybenzyl 7β-phenylacetamido-3-(2-chloroacetyloxy)ethylthio-3-cephem-4-carboxylate, and the solution was cooled to −50° C. To the solution were added 0.706 ml (8.64 mM) of pyridine and 1.196 g (5.76 mM) of phosphorus pentachloride, the reaction temperature of the mixture was raised to 20° C. for a period of one hour, and the mixture was stirred at the same temperature for one hour. Then, the reaction mixture was cooled to −50° C., 10 ml of dry methanol was added, and the temperature of the mixture was raised to 0° C. for a period of one hour. To the reaction mixture cooled to −5° C. was added 10 ml of water, and the mixture was stirred under ice-cooling for 40 minutes. The mixture was made neutral by addition of a saturated aqueous sodium bicarbonate solution, the organic layer was washed with a saturated aqueous sodium chloride solution (10 ml×3) and dried over anhydrous magnesium sulfate. The solvent was evaporated, and the residue was purified by silica gel column chromatography (eluent, dichloromethane) to give 1.22 g of p-methoxybenzyl 7β-amino-3-(2-chloroacetyloxy)ethylthio-3-cephem-4-carboxylate.

(c) In 50 ml of dry dichloromethane was dissolved 2.09 g (3.2 mM) of α-(2-tritylaminothiazole-4-yl)-α-[(Z)-benzhydryloxycarbonylmethoxyimino]acetic acid, and the solution was cooled to −10° C. To the solution were added 1.298 ml (16 mM) of pyridine and 666 mg (3.2 mM) of phosphorus pentachloride, and the mixture was stirred for 20 minutes. And then 1.22 g (2.58 mM) of the 7-amino derivative obtained in the above (b) was added at the same temperature, and the mixture was stirred for 20 minutes. After the reaction, the organic layer was washed with 20 ml of 0.5%, hydrochloric acid and 20 ml of a saturated aqueous sodium chloride solution, successively, and then dried over anhydrous magnesium sulfate. The solvent was evaporated, and the residue was purified by silica gel column chromatography (eluent; benzene: acetone=25:1) to give 1.51 g of p-methoxybenzyl 7β-{α-(2-tritylaminothiazole-4-yl)-

α[(Z)-benzhydryloxycarbonylmethoxyimino]acetamido}-3-(2-chloroacetyloxy)ethylthio-3-cephem-4-carboxylate.

(d-1) To a solution of 1.24 g (1.12 mM) of p-methoxybenzyl 7β-{α-(2-tritylaminothiazole-4-yl)-α-[(Z)-benzhydryloxycarbonylmethoxyimino]acetamido}-3-(2-chloroacetyloxy)ethylthio-3-cephem-4-carboxylate, in 7 ml of N,N-dimethylacetamide was added 171 mg (2.24 mM) of thiourea, and the mixture was stirred at 20° C. for 16 hours. Then, the reaction mixture was poured into 20 ml of ice-water and extracted with 30 ml of ethyl acetate, and the extract was washed with a saturated aqueous sodium chloride solution (10 ml×3) and dried over anhydrous magnesium sulfate. The solvent was evaporated, and the residue was purified by silica gel column chromatography (eluent; benzene:acetone=5:1), and then crystallized from diethyl ether to give 780 mg of p-methoxybenzyl 7β-{α-(2-tritylaminothiazole-4-yl)-α-[(Z)-benzhydryloxycarbonylmethoxyimino]acetamido}-3-(2-hydroxy)ethylthio-3-cephem-4-carboxylate.

(d-2) To a mixture of trifluoroacetic acid (4 ml) and anisole (0.8 ml) was added under ice-cooling 360 mg (0.349 mM) of p-methoxybenzyl 7β-{α-(2-tritylaminothiazole-4-yl)-α-[(Z)-benzhydryloxycarbonylmethoxyimino]acetamido}-3-(2-hydroxy)ethylthio-3-cephem-4-carboxylate, and the mixture was stirred for one hour. The reaction mixture was added slowly dropwise to a mixture of diethyl ether and petroleum ether (1:2, 50 ml), thecrystals which formed were collected by filtration to give 188 mg of 7β-{α-(2-aminothiazole-4-yl)-α-[(Z)-carboxymethoxyimino]acetamido}-3-(2-hydroxy)ethylthio-3-cephem-4-carboxylic acid trifluoroacetate. The crystals and 77 mg (0.917 mM) of sodium bicarbonate were dissolved in 5 ml of water, and the solution was applied to a Sephadex HL-20 column chromatography (eluent: water) to give 164 mg of 7β-{α-(2-aminothiazole-4-yl)-α-[(Z)-carboxymethoxyimino]acetamido}-3-2-hydroxy)ethylthio-3-cephem-4-carboxylic acid sodium salt.

NMR(D$_2$O) δ(ppm): 2.77–3.08(2H, m), 3.58(1H, d, J=17 Hz), 3.75(1H, t, J=6 Hz), 3.82(1H, d, J=17 Hz), 4.60(2H, s), 5.30(1H, d, J=5 Hz), 5.85(1H, d, J=5 Hz), 7.10(1H, s).

IR $\nu_{max}^{KBr}$ cm$^{-1}$; 3200, 1750, 1590, 1340, 1035.

EXAMPLE 27

In 10 ml of dichloromethane was dissolved 400 mg (0.388 mM) of p-methoxybenzyl 7β-{α-(2-tritylaminothiazole-4-yl)-α-[(Z)-benzhydryloxycarbonylmethoxyimino]acetamido}-3-(2-hydroxy)ethylthio-3-cephem-4-carboxylate obtained in Example 26 (d-1), and the solution was cooled to −30° C. To the solution was added dropwise 0.044 ml (0.466 mM) of chlorosulfonyl isocyanate, and the mixture was stirred at −10° C. for 15 minutes. To the reaction mixture was added 5 ml of a 20% aqueous sodium sulfate solution, and the mixture was stirred at 20° C. for one hour. Then the organic layer was washed with a saturated aqueous sodium chloride solution (10 ml×3) and dried over anhydrous magnesium sulfate. The solvent was evaporated and the residue was purified by silica gel column chromatography (eluent; benzene:acetone=7:1) to give 240 mg of p-methoxybenzyl 7β-{α-(2-tritylaminothiazole-4-yl)-α-[(Z)-benzhydryloxycarbonylmethoxyimino]acetamido}-3-(2-carbamoyloxy)ethylthio-3-cephem-4-carboxylate.

(d-2) To a mixture of trifluoroacetic acid (3 ml) and anisole (0.6 ml) was added under ice-cooling 240 mg (0.223 mM) of p-methoxybenzyl 7β-{α-(2-tritylaminothiazole-4-yl)-α-[(Z)-benzhydryloxycarbonylmethoxyimino]acetamido}-3-(2-carbamoyloxy)ethylthio-3-cephem-4-carboxylate, and the mixture was stirred for one hour. The reaction mixture was added slowly dropwise to a mixture of diethyl ether and petroleum ether (1:2, 50 ml), and the crystals which formed were collected by filtration to give 120 mg of 7β-{α-(2-aminothiazole-4-yl)-α-[(Z)-carboxymethoxyimino]acetamido}-3-(2-carbamoyloxy)ethylthio-3-cephem-4-carboxylic acid trifluoroacetate. Subsequently, the crystals and 46 mg (0.548 mM) of sodium bicarbonate were dissolved in 5 ml of water, and the solution was treated by Sephadex LH-20 column chromatography (eluent; water) to give 99 mg of 7β-{α-(2-aminothiazole-4-yl)-α-[(Z)-carboxymethoxyimino]acetamido}-3-(2-carbamoyloxy)ethylthio-3-cephem-4-carboxylic acid sodium salt.

NMR(D$_2$O) δ(ppm); (2.98–3.10(2H, m), 3.57(1H, d, J=17 Hz), 3.86(1H, d, J=17 Hz), 4.10(2H, t, J=6 Hz), 4.59(2H, s), 5.28(1H, d, J=5 Hz), 5.83(1H, d, J=5 Hz), 7.08(1H, s).

IR $\nu_{max}^{KBr}$ cm$^{-1}$; 3300, 1750, 1585, 1530, 1390, 1330, 1060, 1030.

What is claimed is:

1. Cephalosporin derivatives represented by the formula:

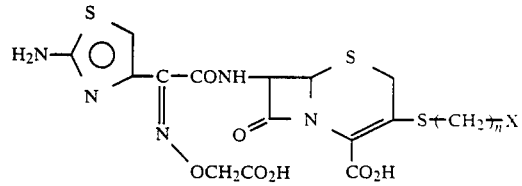

wherein X represents halogen, hydroxyl, cyano, trifluoromethyl, amino, lower alkylcarbonylamino, lower alkoxy, lower alkylthio, lower alkoxycarbonyl, carbamoyl, N,N-dimethylcarbamoyl, N,N-diethylcarbamoyl, N-methylcarbamoyl, N-ethylcarbamoyl, carbamoyloxy, lower alkylcarbonyl, lower alkenyl, ethynyl, thiocyanate or, α-carboxyaminomethyl, and n is an integer of 1 to 3, and the non-toxic, pharmaceutically acceptable salts thereof.

2. A cephalosporin derivative according to claim 1 wherein X is a cyano group.

3. A cephalosporin derivative according to claim 1 wherein X is a carbamoyl group.

4. A cephalosporin derivative according to claim 1 wherein X is a carbamoyloxy group.

5. A cephalosporin derivative according to claim 1 wherein X is a fluorine atom.

6. A cephalosporin derivative according to claim 1 wherein X is an amino group.

7. A cephalosporin derivative according to claim 1 wherein X is a methoxy group.

* * * * *

UNITED STATES PATENT AND TRADEMARK OFFICE
CERTIFICATE OF CORRECTION

PATENT NO. : 4,812,562

DATED : March 14, 1989

INVENTOR(S) : WATANABE et al

It is certified that error appears in the above-identified patent and that said Letters Patent is hereby corrected as shown below:

Column 8, line 19, "ml", second occurrence, should read -- mg --.

Signed and Sealed this

Second Day of January, 1990

Attest:

JEFFREY M. SAMUELS

Attesting Officer     Acting Commissioner of Patents and Trademarks